(12) United States Patent
Hu et al.

(10) Patent No.: US 6,596,450 B2
(45) Date of Patent: Jul. 22, 2003

(54) CHARGE TRANSPORT COMPONENTS

(75) Inventors: Nan-Xing Hu, Oakville (CA); Yu Qi, Mississauga (CA); Ping Liu, Mississauga (CA)

(73) Assignee: Xerox Corporation, Stamford, CT (US)

( * ) Notice: Subject to any disclaimer, the term of this patent is extended or adjusted under 35 U.S.C. 154(b) by 17 days.

(21) Appl. No.: 09/949,329

(22) Filed: Sep. 10, 2001

(65) Prior Publication Data

US 2003/0082468 A1 May 1, 2003

(51) Int. Cl.$^7$ .................................................. G03G 5/047
(52) U.S. Cl. ..................................... 430/58.7; 430/58.75
(58) Field of Search ............................... 430/58.7, 58.75

(56) References Cited

U.S. PATENT DOCUMENTS

| | | | |
|---|---|---|---|
| 3,121,006 A | 2/1964 | Middleton et al. ................ 96/1 |
| 3,871,882 A | 3/1975 | Wiedemann .................... 96/1.5 |
| 4,265,990 A | 5/1981 | Stolka et al. .................. 430/59 |
| 4,555,463 A | 11/1985 | Hor et al. ...................... 430/59 |
| 4,587,189 A | 5/1986 | Hor et al. ...................... 430/59 |
| 4,869,988 A | 9/1989 | Ong et al. ..................... 430/59 |
| 4,946,754 A | 8/1990 | Ong et al. ..................... 430/59 |
| 5,116,703 A | 5/1992 | Badesha et al. ............... 430/59 |
| 5,352,554 A | 10/1994 | Mishima et al. ............... 430/59 |
| 5,436,099 A | * 7/1995 | Schank et al. ............. 430/58.6 |

OTHER PUBLICATIONS

Copending application U.S. Ser. No. 09/770,159, Filed Jan. 26, 2001, on "Organic Light Emitting Devices".
Copending application U.S. Ser. No. 09/770,154, Filed Jan. 26, 2001, on "Electroluminescent Devices".

* cited by examiner

*Primary Examiner*—Mark A. Chapman
(74) *Attorney, Agent, or Firm*—Eugene O. Palazzo

(57) ABSTRACT

A charge transport composition containing aromatic amines with crosslinkable silanes as represented by the formula

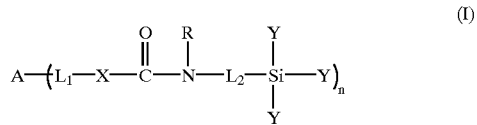

(I)

wherein A represents a hole transporting aromatic tertiary amine moiety; $L_1$ and $L_2$ represents charge such as a divalent group; X represents oxygen or an imino group; Y represents an alkoxy group, or a halide atom; R is a hydrogen atom or an alkyl group; and n represents the number of repeating segments.

16 Claims, No Drawings

CHARGE TRANSPORT COMPONENTS

COPENDING APPLICATIONS

Charge transport crosslinkable aromatic amines with silane functionalities and which components are resistant at high temperatures, such as 75° C. to 100° C., and moreover, which components can be selected for incorporation into solar cell, and EL devices, are illustrated for example in applications U.S. Ser. No. 09/770,159, and U.S. Ser. No. 09/770,154, the disclosures of which are totally incorporated herein by reference. More specifically, illustrated in these applications is an organic light emitting device comprising in an optional sequence (i) a substrate;
(ii) a first electrode;
(iii) a mixed region comprising a mixture of a hole transport material and an electron transport material, and wherein this mixed region includes at least one organic luminescent material;
(iv) a second electrode;
(v) a thermal protective element coated on the second electrode, wherein one of the two said first and second electrodes is a hole injection anode, and one of the two said electrodes is an electron injection cathode, and wherein the organic light emitting device further comprises;
(vi) a hole transport region, interposed between the anode and the mixed region, wherein the hole transport region optionally includes a buffer layer; and
(vii) an electron transport region interposed between the second electrode and the mixed region; and an organic light emitting device comprising in sequence
a substrate;
a first electrode;
a light emitting region comprising an organic luminescent material; and
a second electrode, and a thermal protective element.

BACKGROUND OF THE INVENTION

The present invention is directed generally to novel charge transport components and imaging members thereof, such as photoconductive imaging members, comprised of photogenerating layers and charge transporting aromatic amines with crosslinkable silane functionalities that are readily prepared and which amines possess an electronic purity in embodiments.

The imaging members of the present invention can be selected for imaging and printing machines, such as the Xerox Corporation Docucolor products.

A problem with a number of current photoreceptors is short operational life caused primarily by mechanical abrasion of the photoreceptor surface. This abrasion is especially severe when bias-charging roll (BCR) is used as the charging device, as the photoreceptor surface is subject to severe chemical attacks from the corrosive species generated during charging. For example, the photoreceptor life when BCR charging is utilized and a polycarbonate Z transport layer binder is generally a low of about 150,000 to 250,000 revolution cycles.

One approach to reduce the aforementioned abrasion of the photoreceptor surface is to apply a crosslinked top layer on the photoreceptor by, for example, sol-gel process or by polycondensation, and wherein the crosslinkable siloxane polymeric materials can be selected as the charge transport layer and to provide some wear resistance to the photoreceptor surface. These silane-crosslinkable charge transport aromatic amines have been synthesized from the hydrosilation of alkene-functionalized aromatic amines or from the reaction of aromatic amine-functionalized carboxylic derivatives with amino or hydroxy-functionalized silanes, reference U.S. Pat. No. 5,352,554, the disclosure of which is totally incorporated herein by reference. However, the silane-containing aromatic amines prepared from those processes are generally difficult to purify to electronic grade process because of the reactive nature of the silane groups. With the processes of the present invention in embodiments, there can be generated a series of electronic grade novel aromatic amines with crosslinkable silane functionalities of the Formula (I) that can be readily obtained with electronic grade. A precursor in generating the aromatic amines of the Formula (I) is the hydroxy or amino-functionalized aromatic amines of Formula (II), which can be prepared from Ullmann reactions and can be readily purified to electronic grade, such as 100 percent purity, by conventional procedures. Since the hydroxy or amino-functionalized aromatic amines of Formula (II) react with an isocyanato-silane of Formula (III) very little if any byproducts result thereby enabling electronic purity for the resulting product.

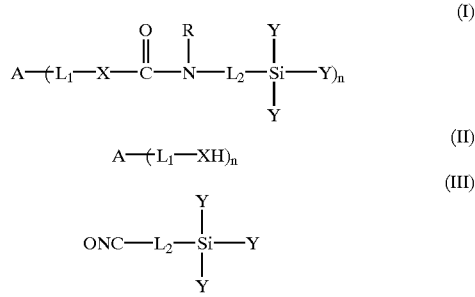

wherein A represents a hole transporting aromatic tertiary amine moiety; $L_1$ and $L_2$ represents a divalent group of an alkylene, or a substituted alkylene of, for example, from 1 to about 10 carbon atoms, such as methylene, ethylene, propylene and butylene; X represents oxygen or an imino group; Y represents an alkoxy group or a halide, for example methoxy, ethoxy, propoxy, isopropoxy, chlorine and bromide; R is a hydrogen atom or an alkyl group of from 1 to about 5 carbon atoms; and n is an integer or number of from 1 to about 5.

PRIOR ART

Generally, layered photoresponsive imaging members are described in a number of U.S. patents, such as U.S. Pat. No. 4,265,990, the disclosure of which is totally incorporated herein by reference, wherein there is illustrated an imaging member comprised of a photogenerating layer, and an aryl amine hole transport layer. For example, charge transport layers comprised of aryl diamines dispersed in polycarbonates like MAKROLON® are known. Examples of photogenerating layer components include trigonal selenium, metal phthalocyanines, vanadyl phthalocyanines, and metal free phthalocyanines. Additionally, there is described in U.S. Pat. No. 3,121,006 a composite xerographic photoconductive member comprised of finely divided particles of a photoconductive inorganic compound dispersed in an electrically insulating organic resin binder.

There are disclosed in U.S. Pat. No. 3,871,882 photoconductive substances comprised of specific perylene-3,4,9,10- tetracarboxylic acid derivative dyestuffs. In accordance with the teachings of this patent, the photoconductive layer is preferably formed by vapor depositing the dyestuff in a vacuum. Also, there is disclosed in this patent dual layer photoreceptors with perylene-3,4,9,10-tetracarboxylic acid diimide derivatives, which have spectral response in the wavelength region of from 400 to 600 nanometers. Further, in U.S. Pat. No. 4,555,463, the disclosure of which is totally incorporated herein by reference, there is illustrated a layered imaging member with a chloroindium phthalocyanine photogenerating layer and an aryl amine charge transport layer. In U.S. Pat. No. 4,587,189, the disclosure of which is totally incorporated herein by reference, there is illustrated a layered imaging member with a nonhalogenated perylene pigment photogenerating component and an aryl amine charge transport layer. Both of the aforementioned patents disclose an aryl amine molecule components as a hole transport layer, and wherein there can be selected a number of resin binders.

In U.S. Pat. No. 4,869,988 and U.S. Pat. No. 4,946,754, the disclosures of which are totally incorporated herein by reference, there are described layered photoconductive imaging members with transport layers incorporating, for example, biarylyl diarylamines, N,N-bis(biarylyl)anilines, and tris(biarylyl)amines as charge transport compounds. More specifically, in the above-mentioned patents, there are disclosed layered photoconductive imaging members comprised of a supporting substrate, a photogenerating layer optionally dispersed in an inactive resinous binder, and in contact therewith a charge transport layer comprised of the above-mentioned charge transport compounds, or mixtures thereof dispersed in a number of resinous binders.

It is also indicated in the aforementioned patents that there may be selected as resin binders for the charge transport molecules those components as illustrated in U.S. Pat. No. 3,121,006 including polycarbonates, polyesters, epoxy resins, polyvinylcarbazole; and also wherein for the preparation of the charge transport layer with a polycarbonate there is selected methylene chloride as a solvent.

Although imaging member devices with various charge transport layers, especially hole transport layer materials with hole transport molecules including aryl amines dispersed in resinous binders, such as polycarbonates have been disclosed in the prior art, and are suitable for their intended purposes, a need remains for improved imaging members, particularly layered members, with chemically and mechanically robust transport layers, and wherein the devices incorporating certain charge transport components exhibit extended lifetimes, such as about 1,000,000 imaging cycles. Further, there continues to be a need for layered imaging members wherein the layers are sufficiently adhered to one another to allow the continuous use of such members in repetitive imaging systems. Also, there continues a need for improved layered imaging members comprised of hole transport layers wherein the problems of transport molecule crystallization, bleeding and leaching are avoided or minimized. Furthermore, there is a need for imaging members which can be fabricated from nontoxic solvents, and wherein the resulting imaging members are inert to the users thereof. A further need resides in the provision of photoconductive imaging members with desirable mechanical characteristics, and excellent photoinduced discharge core characteristics. These and other needs may be accomplished, it is believed, in embodiments of the present invention.

Another need resides in the provision of imaging members containing charge transport layers with acceptable xerographic electrical performance including higher charge acceptance, lower dark decay, increased charge generation efficiency, reduced residual charge and/or reduced erase energy, improved long-term cycling performance, and less variability in performance with respect to environmental changes in temperature and relative humidity. There is also a need for imaging members with enhanced photosensitivity in the red region of the light spectrum, enabling the resulting imaging members thereof to be selected for imaging with red diodes and gas lasers. Furthermore, there is a need for members with spectral response in the green and blue regions of the spectrum to enable imaging by newly emerging blue and green electronic imaging light sources. These and other needs may be accomplished, it is believed, in embodiments of the present invention.

With respect to the prior art, only a small part thereof has been selected and this part may or may not be fully representative of the prior art teachings or disclosures.

SUMMARY OF THE INVENTION

Examples of features of the present invention include:

It is a feature of the present invention to provide charge transport components for EL devices, solar cells, photoconductive imaging members and other devices which each contain aromatic amines with crosslinkable silane functionalities.

It is another feature of the present invention to provide a process for preparing the novel aromatic amines with crosslinkable silane functionalities.

It is another feature of the present invention to provide extended life imaging members containing aromatic amines with crosslinkable silane functionalities.

It is another feature of the present invention to provide extended life photoconductive imaging members with photosensitivity in both the visible and infrared wavelength regions of the light spectrum, such as from about 400 to about 900 nanometers.

Aspects of the present invention relate to a composition comprised of aromatic amines with crosslinkable silanes, which composition can be represented by the following Formula I

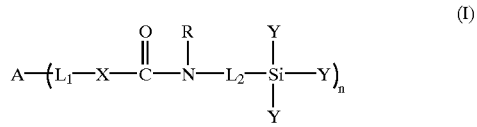

(I)

wherein A is a hole transporting aromatic tertiary amine moiety; $L_1$ and $L_2$ represent independently a divalent group of, for example, an alkylene or a substituted alkylene; X is oxygen or an imino group; Y is an alkoxy group containing, for example, from 1 to about 6 carbon atoms, or a halide atom; R is a hydrogen atom or an alkyl group; and n is a number of from 1 to about 5; a composition wherein $L_1$ and $L_2$ are independently selected from the group consisting of methylene, ethylene, propylene, butylene and pentylene; a composition wherein A is selected from the group consisting of
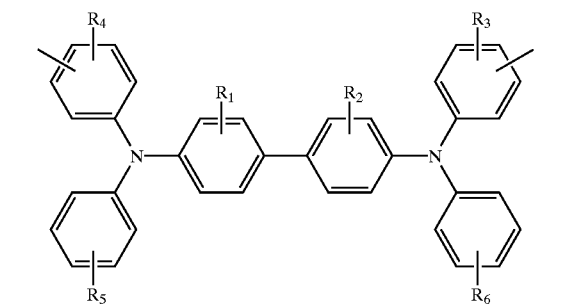
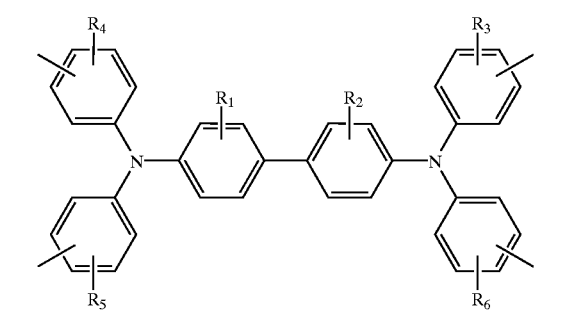
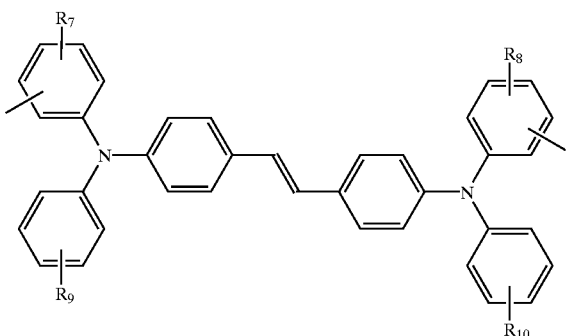
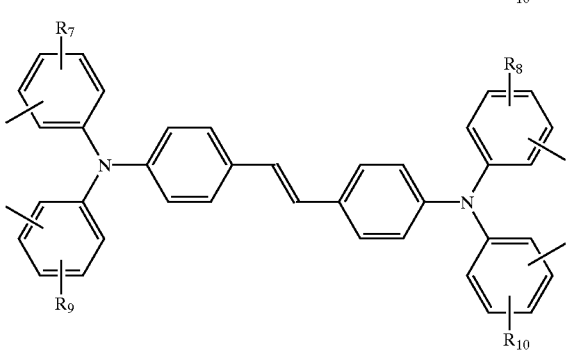
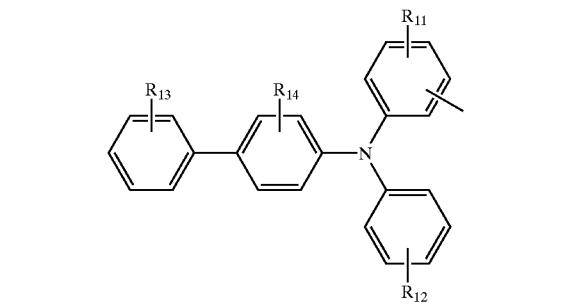
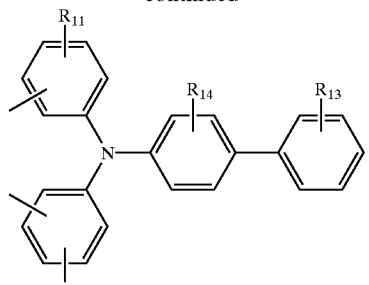
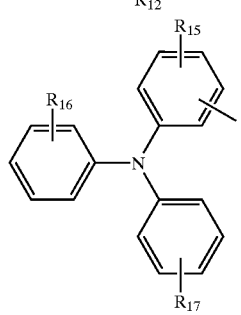
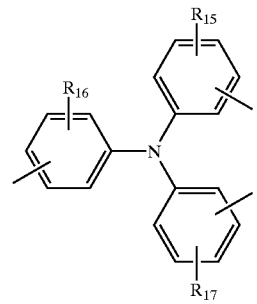
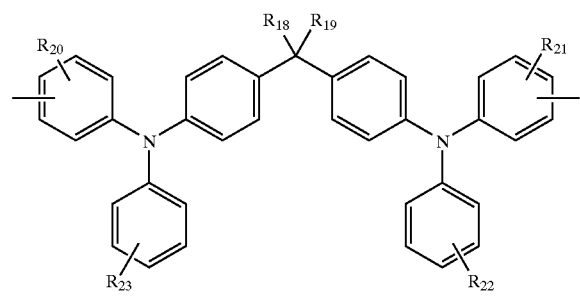
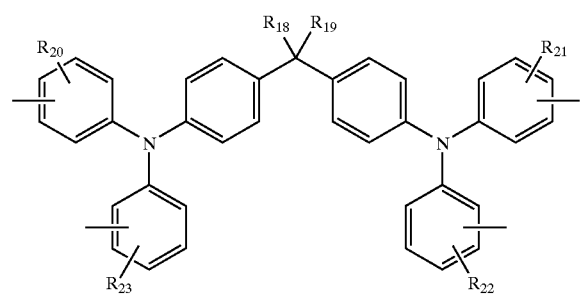
wherein $R_1$ to $R_{23}$ are independently a hydrogen atom, an alkyl with from 1 to about 10 carbon atoms, a cyclic alkyl with from 1 to about 10 atoms, an alkoxyl group with from 1 to about 5 carbon atoms, or a halogen; a composition wherein X is an oxygen atom; a composition wherein X is an imino group; a composition wherein Y is selected from the group consisting of methoxy, ethoxy, propoxy, and isopropoxy; a composition wherein Y is selected from the group consisting of chloride and bromide; a composition wherein R is a hydrogen atom; a photoconductive imaging member comprised of charge transport composition comprised of a hole transport segment of Formula (IV)

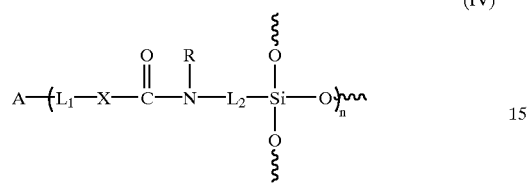

(IV)

wherein A represents a hole transporting aromatic tertiary amine moiety; $L_1$ and $L_2$ represents a divalent group of an alkylene; X represents oxygen or an imino group; R is a hydrogen atom or an alkyl group; and n represents the number of repeating segments; a member wherein $L_1$ and $L_2$ are independently selected from the group consisting of methylene, ethylene, propylene, butylene and pentylene; a photoconductive member containing the above composition wherein A is selected from the group consisting of

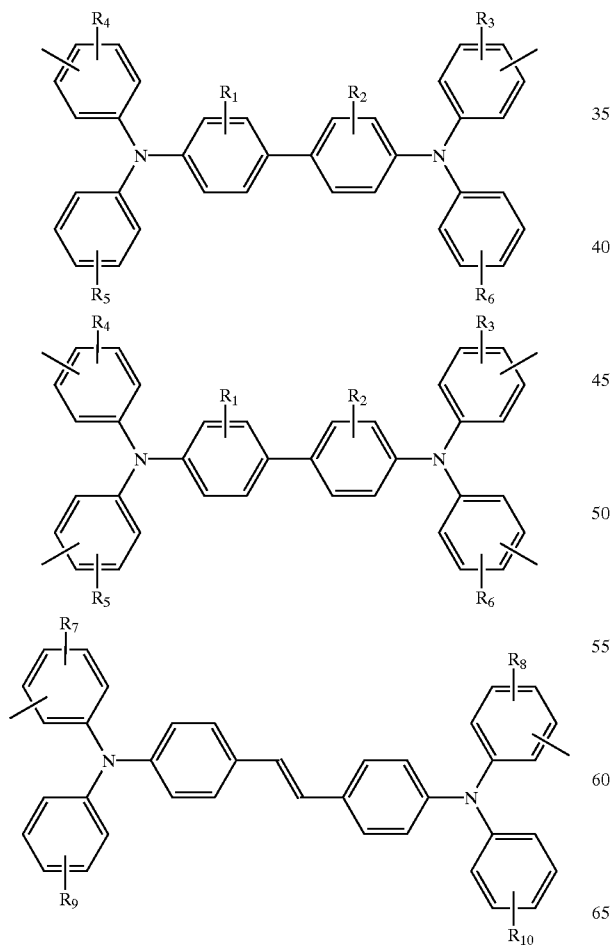

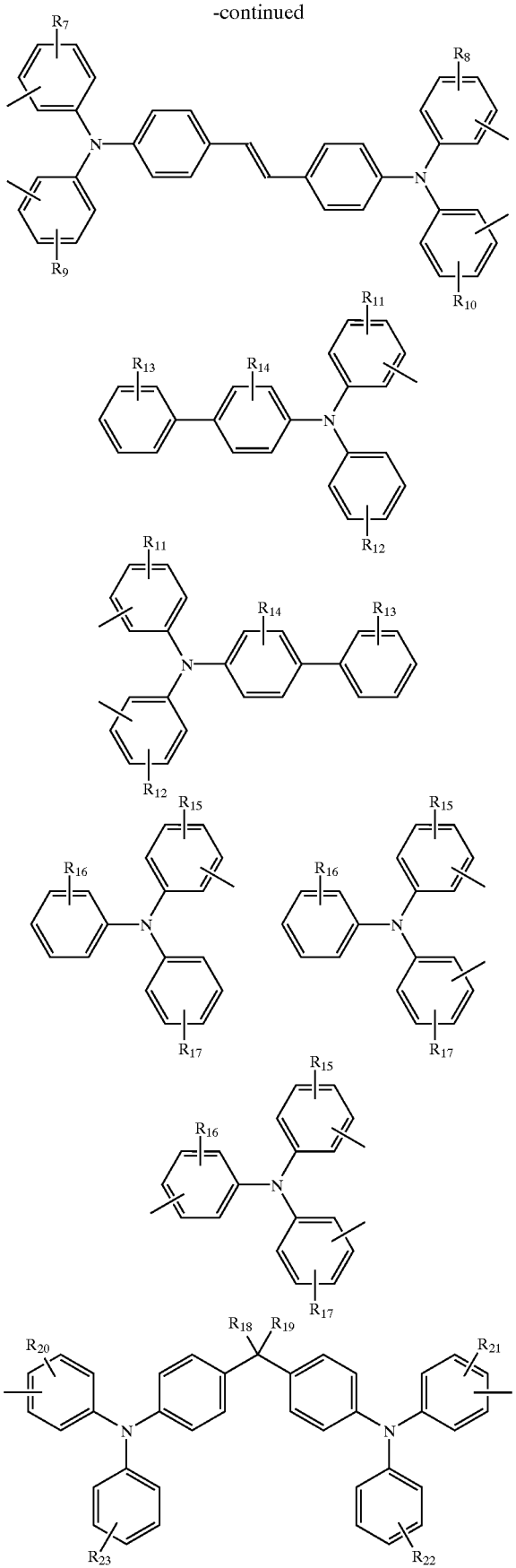

-continued

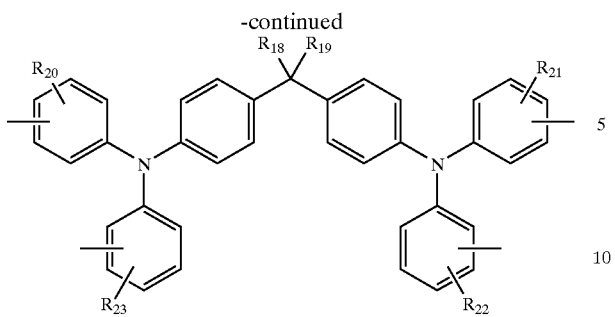

wherein $R_1$ to $R_{23}$ are independently a hydrogen atom, an alkyl with from 1 to about 12 carbon atoms, a cyclic alkyl with from 1 to about 12 atoms, an alkoxyl group with from 1 to about 7 carbon atoms, or a halogen; a member wherein X is an oxygen atom, or wherein X is an imino group, and wherein R is a hydrogen atom; a photoconductive imaging member comprised of a photogenerating layer and a charge transport layer, and wherein the charge transport layer is comprised of a hole transport composition comprised of an amine of Formula (IV)

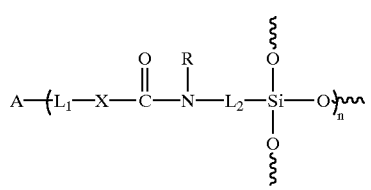

(IV)

wherein A represents a charge transporting aromatic tertiary amine moiety; $L_1$ and $L_2$ represents a divalent group of an alkylene, optionally with from 1 to about 10 carbon atoms; X represents oxygen or an imino group; R is a hydrogen atom or an alkyl group optionally with from 1 to about 5 carbon atoms; and n is a number; a photoconductive imaging member wherein $L_1$ and $L_2$ are independently selected from the group consisting of methylene, ethylene, propylene, butylene and pentylene, and n is from 1 to about 5; a photoconductive imaging member comprised of a photogenerating layer and a charge transport layer containing aromatic amines with crosslinkable silane functionalities and which amines are represented by the following formula

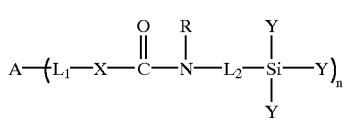

(I)

wherein A represents a hole transporting aromatic tertiary amine moiety; $L_1$ and $L_2$ represents a divalent group of an alkylene, or a substituted alkylene with, for example, from 1 to about 10 carbon atoms, such as methylene, ethylene, propylene and butylene; X represents oxygen or an imino group; Y represents an alkoxy group or a halide, for example methoxy, ethoxy, propoxy, isopropoxy, chloride and bromide; R is a hydrogen atom or an alkyl group with, for example, from 1 to about 5 carbon atoms; and n is an integer from about 1 to about 5; a photoconductive imaging member containing a hole transport as illustrated herein wherein A is selected from the group consisting of

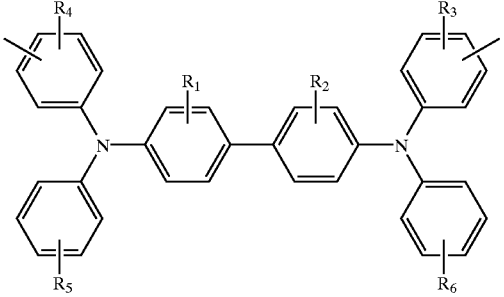

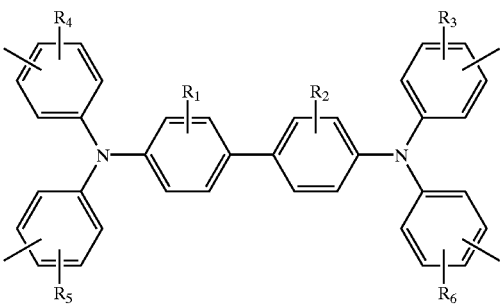

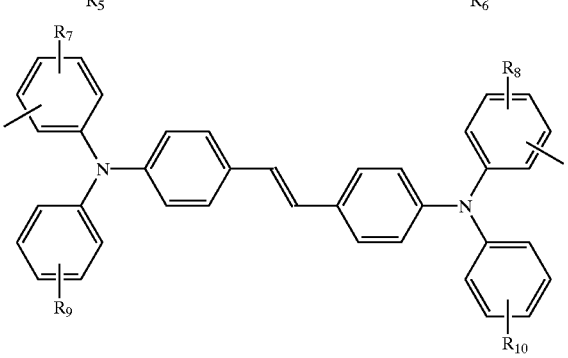

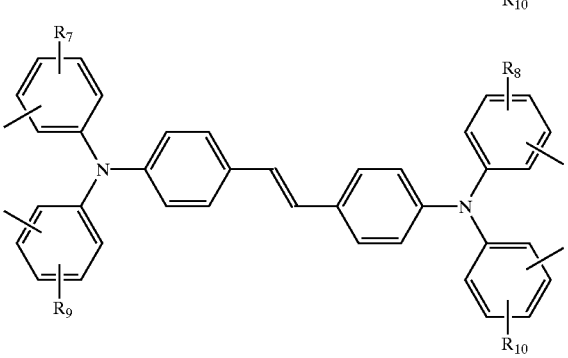

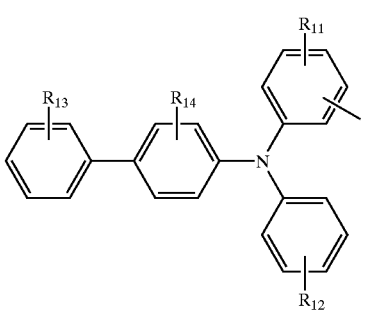

-continued

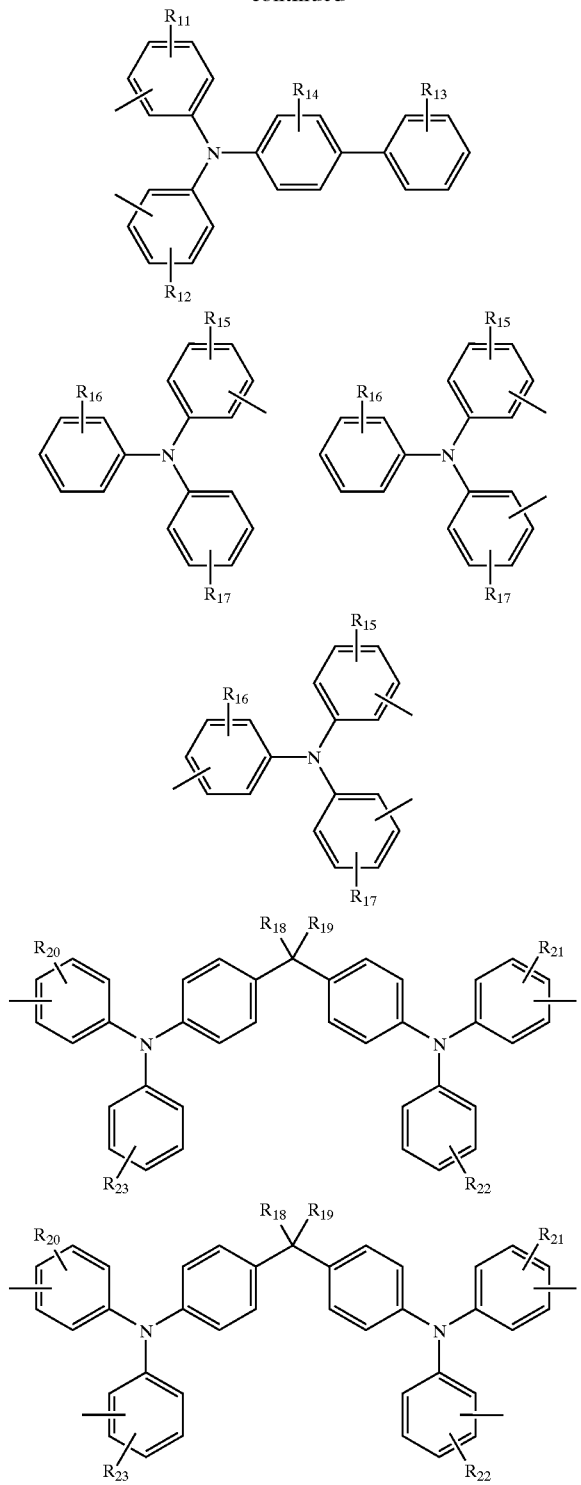

wherein $R_1$ to $R_{23}$ are independently a hydrogen, an alkyl with from 1 to about 10 carbon atoms, a cyclic alkyl with from 1 to about 10 carbon atoms, an alkoxyl group with from 1 to about 7 carbon atoms, or halide; a photoconductive imaging member wherein X is an oxygen atom, or wherein X is an imino group, and wherein R is a hydrogen atom; a photoconductive imaging member containing a hold trans port of the formulas illustrated herein and is comprised of the condensation reaction product of a) a tertiary amine of Formula (I),
b) a crosslinkable silane component, and
c) an optional polymer binder; a photoconductive imaging member wherein the silane is selected from the group consisting of tetraethoxysilicate, 3-aminopropyltrimethoxysilane, 3-aminopropyl triethoxysilane, 3-aminopropyltriisopropoxysilane, 1,2-bis(trimethoxysilyl)ethane, and 1,2-bis (triethoxysilyl)ethane; a photoconductive imaging member wherein said polymer binder is comprised of

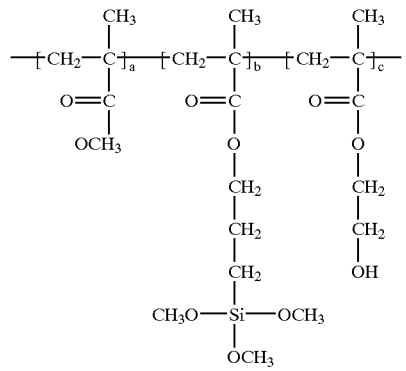

photoconductive imaging member wherein the photogenerating layer is comprised of photogenerating pigments of metal phthalocyanines, metal free phthalocyanines, perylenes, titanyl phthalocyanines, selenium, or hydroxygallium phthalocyanines optionally dispersed in a resin binder; a photoconductive imaging member containing a supporting substrate in contact with the photogenerating layer, or containing a supporting substrate in contact with the charge transport layer; a process for the synthesis of hole transport molecules of Formula I

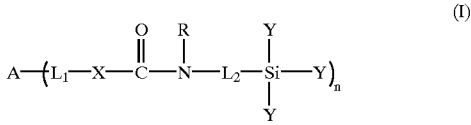

(I)

which comprises the reaction of

(II)

(III)

wherein A represents a hole transporting aromatic tertiary amine moiety; $L_1$ and $L_2$ represents a divalent group of an alkylene, or a substituted alkylene; X represents oxygen or an imino group; Y represents an alkoxy group, or a halide atom; R is a hydrogen; and n represents the number of repeating segment; a process wherein the reaction is conducted at from about 100° C. to about 180° C., optionally in an inert organic solvent; a process wherein said organic solvent is selected from the group consisting of chlorobenzene, toluene, dichlorobenzene, xylene and tetralene; a process wherein the reaction is conducted in the presence of a catalyst selected from the group consisting of a trialkyl amine, a pyridine, a dialkylaminopyridine, and an organic tin compound; a photoconductive imaging member wherein the supporting substrate is a metal, a conductive polymer, or an insulating polymer, each with a thickness of from about 30 microns to about 300 microns optionally overcoated with an electrically conductive layer with an optional thickness of from about 0.01 micron to about 1 micron, and wherein there is further optionally included an overcoating polymer top layer on thr member; a photoconductive imaging member wherein the photogenerating layer is of a thickness of from about 0.2 to about 10 microns, wherein the charge transport layer is of a thickness of from about 10 to about 100 microns, and wherein there is included a supporting substrate overcoated with a polymeric adhesive layer of a thickness of from about 0.01 to about 1 micron; a composition of the appropriate formulas illustrated herein wherein the composition functions as a charge transport in a photoconductive imaging member; and a composition wherein the charge transport is a hole transport; a composition wherein alkylene or substituted alkylene contains from 1 to about 12 carbon atoms; alkoxy contains from 1 to about 12 carbon atoms; and n is 1, 2, or 3.

Illustrated examples of A can be selected from the following

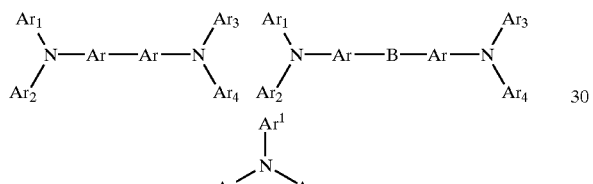

wherein $Ar_1$ to $Ar_4$ are aromatic groups such as phenyl, substituted phenyl, biphenyl, terphenyl, naphthyl, substituted naphthyl, and the like, Ar is a divalent arylene group such as phenylene, substituted phenylene, and the like; B is a divalent linkage, such as vinyl and the like. Specific examples of A are

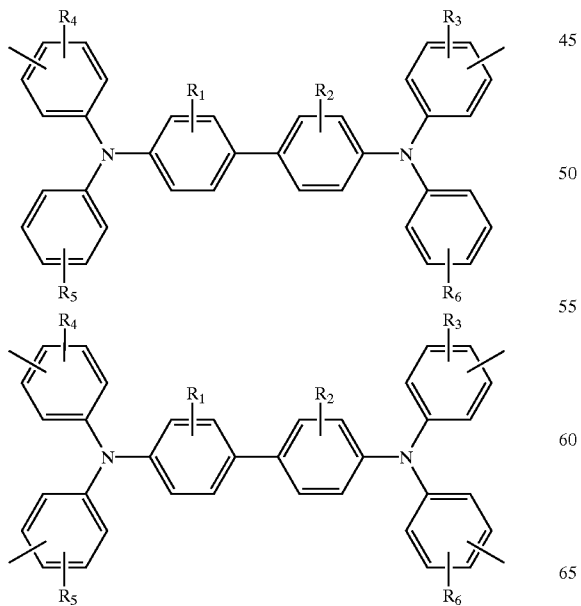

-continued

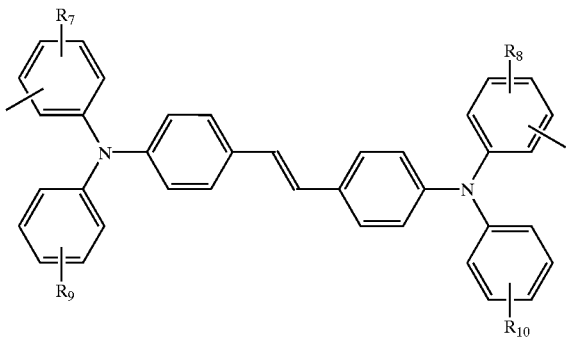

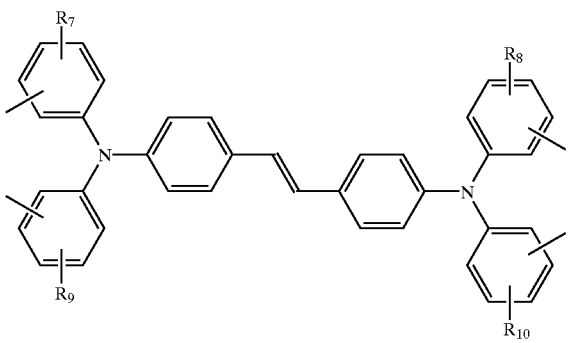

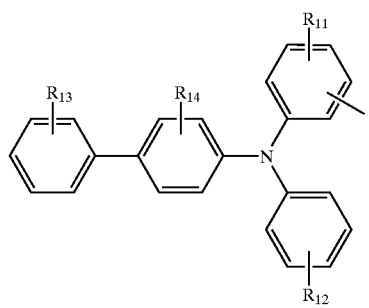

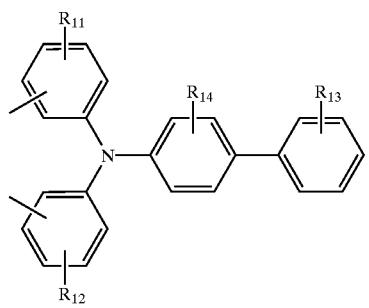

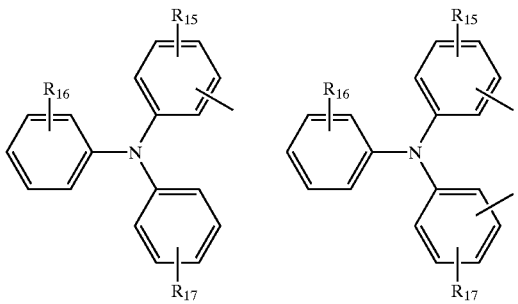

-continued

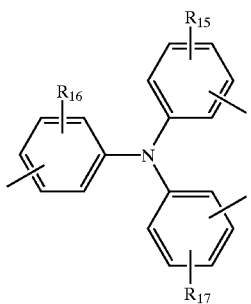

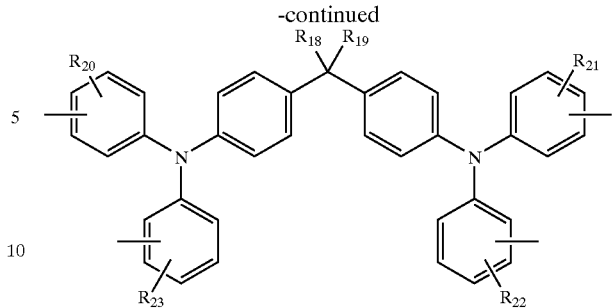

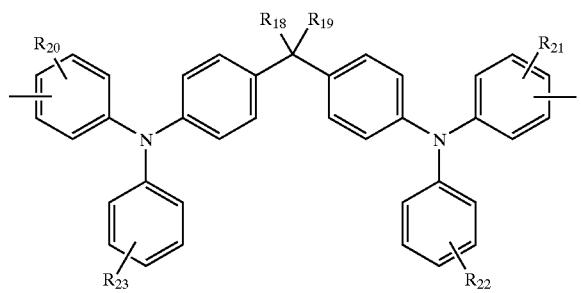

wherein $R_1$ to $R_{23}$ are independently selected from a hydrogen atom, an alkyl, a cyclic alkyl, and a halogen atom, for example, alkyl groups containing from 1 to about 25 carbon atoms, cyclohexyl groups, a chloride, or a bromide.

Specific examples of aromatic amines A include N,N'-biphenyl-N,N'-bis(alkylphenyl)-(1,1'-biphenyl)4,4'-diamine wherein alkyl is, for example, methyl, ethyl, propyl, n-butyl, or the like; N-phenyl-N-alkylphenyl-N-biphenylamine wherein alkyl is, for example, methyl, ethyl, propyl, n-butyl, or the like; tri-alkylphenylamine wherein alkyl is, for example, methyl, ethyl, propyl, n-butyl, or the like; or N,N'-biphenylstilbene-N,N'-bis(alkylphenyl)-(1,1'-biphenylstilbene)-4,4'-diamine wherein alkyl is, for example, methyl, ethyl, propyl, n-butyl, or the like.

Specific examples of aromatic amines with crosslinkable silane functionalities are represented by Formulas (Ia) to (II).

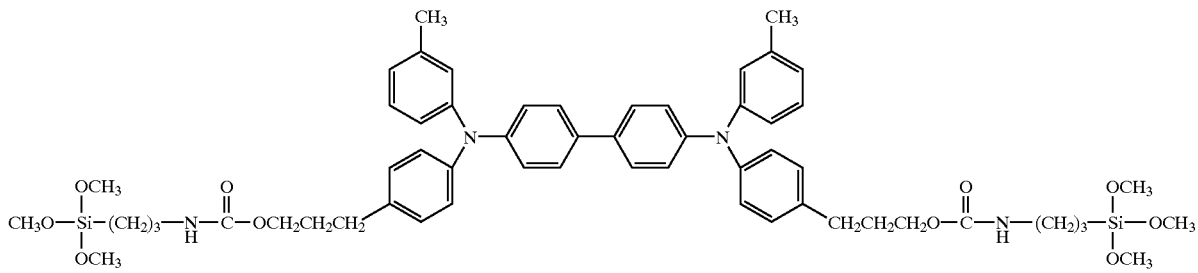
(Ia)

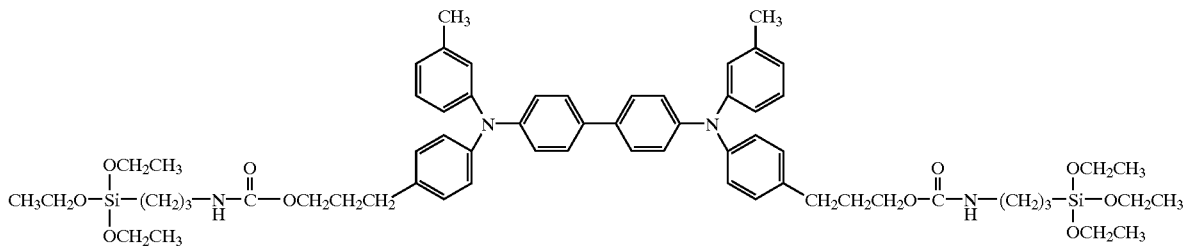
(Ib)

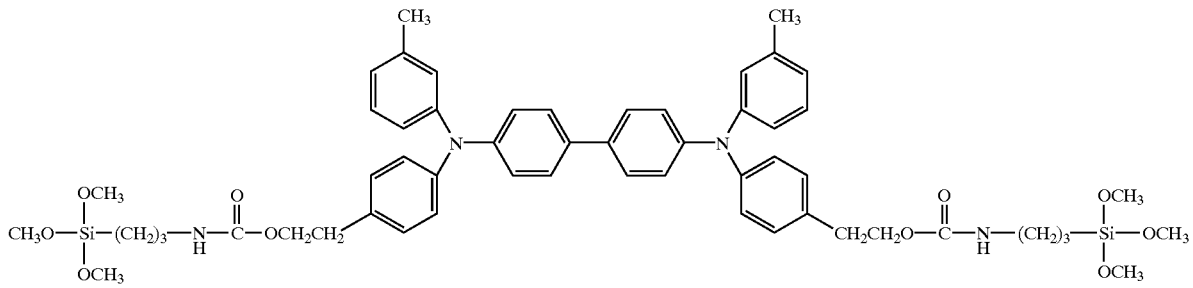
(Ic)

(Id)
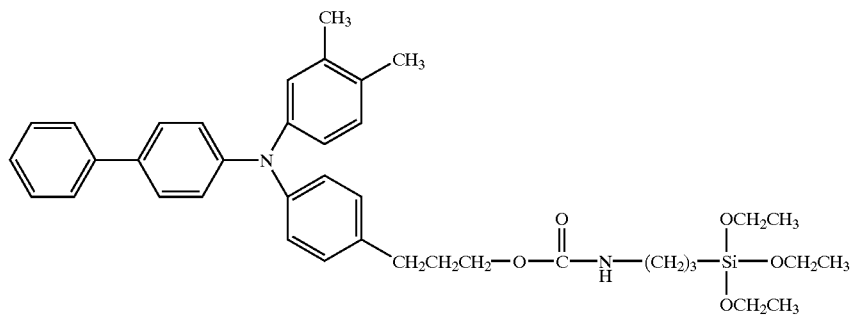
(Ie)
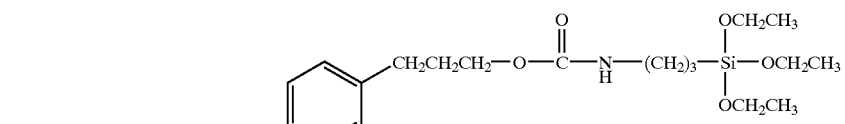
(If)
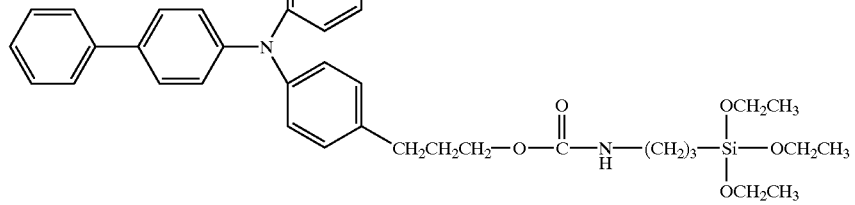
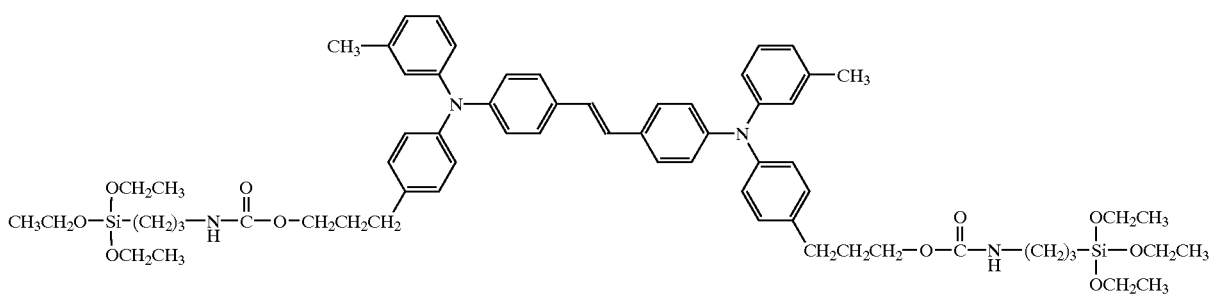
(Ig)
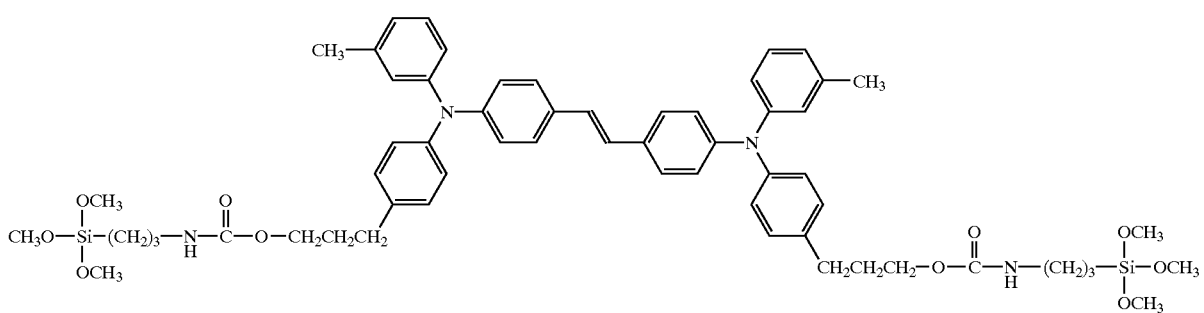
(Ih)
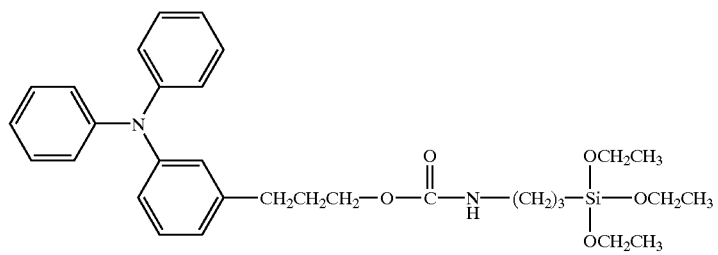

-continued

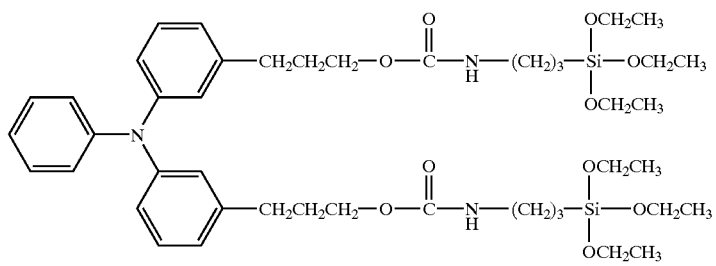

(Ii)

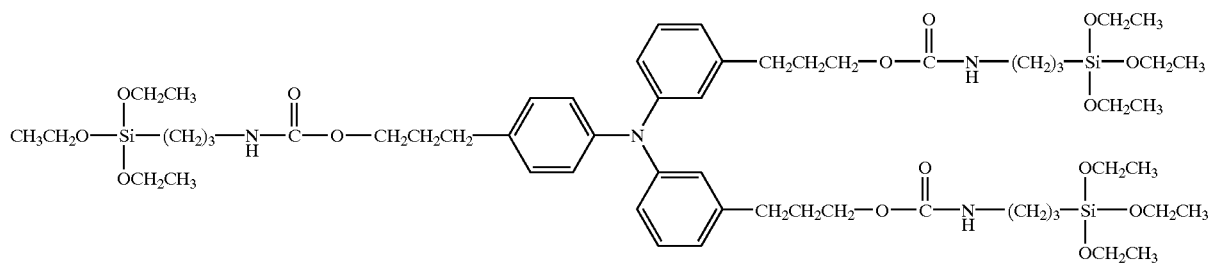

(Ij)

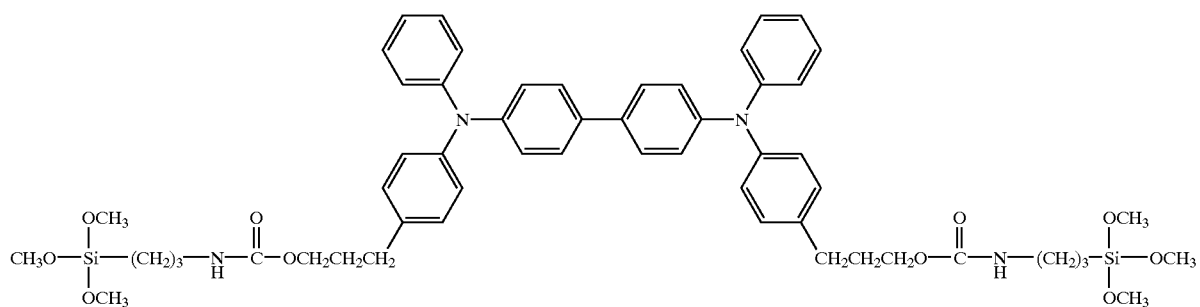

(Ik)

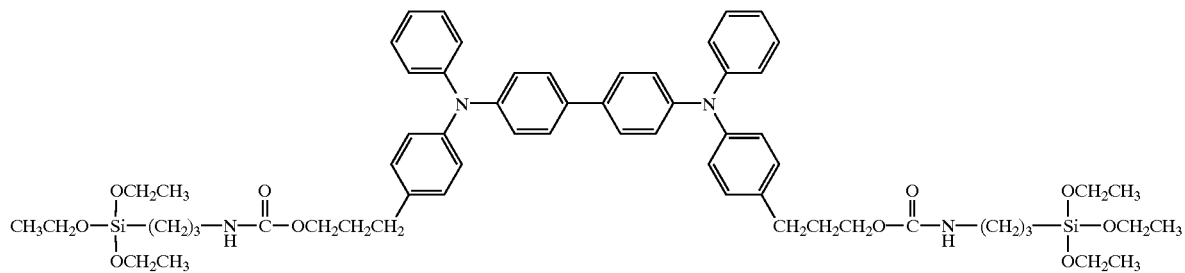

(Il)

Examples of specific precursors selected for the preparation of the aromatic amines of Formula (I) are the hydroxy or amino-functionalized aromatic amines of Formula (II, which can be prepared from Ullmann reactions and can be readily purified to electronic grade by conventional procedures. Since the hydroxy or amino-functionalized aromatic amines of Formula (II) react with an isocyanato-silane of Formula (III), and wherein byproducts are not usually formed, and the resulting silane-containing aromatic amines can be readily obtained with electronic purity.

$$A\text{---}(L_1\text{---}XH)_n \qquad (II)$$

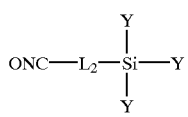

More specifically, the aromatic amines with crosslinkable silane functionalities can be prepared from the reaction of a hydroxy or amino functionalized aromatic amine with an isocyanato-silane in accordance with the following reaction sequence, as illustrated in Scheme 1, and wherein the substituents are as illustrated herein, and wherein, for example, the electronically pure, about 99.5 to about 100 percent, hydroxy or amino functionalized aromatic amine was dissolved in an organic solvent such as chlorobenzene or dichlorobenezene. The isocyanato-silane was then added to the solution. The mixture was heated at a temperature of from about 60° C. to about 200° C., or from about 100° C. to about 180° C. The reaction time was generally from about 5 hours to about 24 hours, or from about 6 hours to 24 hours. After the reaction mixture was cooled to 25° C., another organic solvent such as hexane was added. When the mixture was cooled to about −4° C. to about 0° C. for about 2 hours to about 12 hours, a white crystalline product was formed and collected by filtration. The resulting product, aromatic amine with crosslinkable silane functionalities with electronic purity, was dried in vacuo for 24 hours. The structure of the aromatic amines with crosslinkable silane functionalities was confirmed by NMR and IR spectroscopy.

Scheme 1

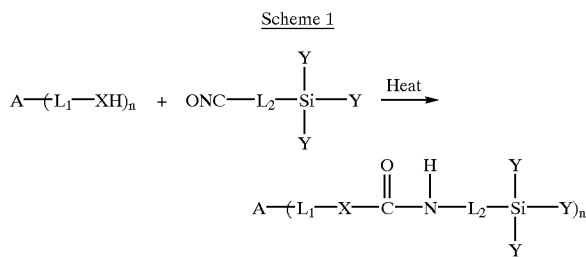

The aromatic amines with crosslinkable silane functionalities of the present invention may be used in various layers of photoresponsive imaging members. For example, they may be selected from charge transport layers or overcoating layers. The resulting imaging member layers containing the aromatic amines with crosslinkable silane functionalities can be prepared either by sol-gel process with a metal alkoxide or mixture of metal alkoxides, reference U.S. Pat. No. 5,116,703, the disclosures of which are totally incorporated herein by reference, or by polycondensation of the silane crosslinkable aromatic amines with a reactive resin binder. The aromatic amines with crosslinkable silane functionalities are present, for example, in an amount of from about 25 to about 80 weight percent, and the total amount of the binder or other components and the charge transport component equals about 100 percent; or wherein the hole transport binder or other components is present in an amount of from about 20 to about 75 weight percent, and the total amount of the binder or other components and the charge transport molecules equals about 100 percent.

A thin film of the charge transport layer or the overcoat layer containing the aromatic amines with crosslinkable silane functionalities can be prepared by mixing the silane-crosslinkable aromatic amine or mixtures thereof of other organoalkoxysilanes with a metal alkoxide or mixture of metal alkoxides, for example tetraalkoxyorthosilicate, and optionally with a silano-crosslinkable resin binder. The mixture is hydrolyzed, condensed and dried to form a polymeric network containing the siloxane-crosslinked charge transporting aromatic amines, as illustrated in Formula (IV).

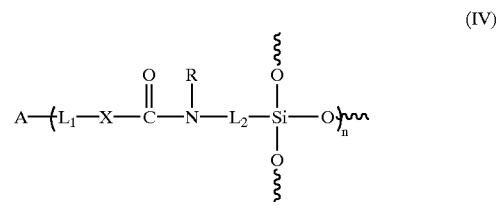

wherein A represents a hole transporting aromatic tertiary amine moiety; $L_1$ and $L_2$ represents independently a divalent group of an alkylene or a substituted alkylene with, for example, from 1 to about 10 carbon atoms; X represents oxygen or an imino group; Y represents an alkoxy group containing from 1 to about 6 carbon atoms, or a halide atom; R is a hydrogen atom or an alkyl group of from 1 to about 5 carbon atoms; and n is an integer of from 1 to about 5.

Examples of photogenerating pigments include metal phthalocyanines, metal free phthalocyanines, perylenes, titanyl phthalocyanines, selenium, hydroxygallium phthalocyanines, and other known photogenerating pigments, and wherein the photogenerating pigments can be optionally dispersed in a resin binder, and wherein the photoconductive imaging member contain a supporting substrate in contact with the photogenerating layer, or containing a supporting substrate in contact with the charge transport layer; a photoconductive imaging member wherein the supporting substrate is a metal, a conductive polymer, or an insulating polymer, each with a thickness of from about 30 microns to about 300 microns optionally overcoated with an electrically conductive layer with an optional thickness of from about 0.01 micron to about 1 micron; or a photoconductive imaging member wherein there is further optionally included an overcoating polymer top layer on the member; a photoconductive imaging member wherein the photogenerator layer component is dispersed in a resinous binder in an amount of from about 5 percent to about 95 percent by weight, and optionally wherein the resinous binder is a polyester, a polyvinylcarbazole, a polyvinylbutyral, a polycarbonate, a polyether carbonate, an aryl amine polymer, a styrene copolymer, or a phenoxy resin; a photoconductive imaging member wherein the charge transport layer is comprised of aromatic amines with crosslinkable silane sites; a photoconductive imaging member wherein the photogenerating layer is of a thickness of from about 0.2 to about 10 microns, wherein the charge transport layer is of a thickness of from about 10 to about 100 microns, and wherein there is included a supporting substrate overcoated with a polymeric adhesive layer of a thickness of from about 0.01 to about 1 micron; a photoconductive imaging method comprising the formation of a latent image on the photoconductive imaging member of the present invention, developing the image with a toner composition comprised of resin and colorant, transferring the image to a substrate, and optionally fixing the image thereto; and the like.

Specific embodiments of the invention will now be described in detail. These Examples are intended to be illustrative, and the invention is not limited to the materials, conditions, or process parameters set forth in these embodiments. All parts and percentages are by weight unless otherwise indicated.

EXAMPLE I

Synthesis of N-Phenyl-N-dimethylphenyl-N-biphenylamino-propanol Methylhydrocinnamate

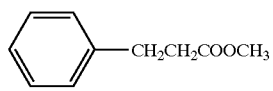

Hydrocinnamic acid (30.04 grams, 0.2 mol) was dissolved in 200 milliliters of methanol in a 500 milliliter round-bottomed flask equipped with a condenser, followed by the addition of 6 grams (0.03 mol) of concentrated sulfuric acid. The mixture was heated at reflux for 6 hours. After the esterification was complete, the reaction mixture was cooled to room temperature, about 25° C. throughout the Examples, then poured over ice. The mixture was stirred and the resulting solid was collected by filtration. The resulting solid was washed with sodium bicarbonate solution and water to a pH 7. The above ester product was dried at 60° C. overnight resulting in 30.65 grams (93.3 percent).

4-Iodo-methyl Hydrocinnamate

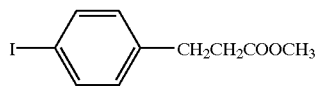

Methyl hydrocinnamate (16.42 grams, 0.1 mol) was dissolved in 100 milliliters of toluene in a 250 milliliter round-bottomed flask equipped with a condenser, followed by the addition of 25.38 grams (0.1 mol) of 9En iodine. The mixture was heated at reflux for 6 hours, cooled to room temperature (25° C.) and set for crystallization for 12 hours. The crystalline product was collected by filtration. The above product was recrystallized in cyclohexane and dried at 60° C. overnight resulting in 24.63 grams (84.9 percent).

N-Biphenyl-N-dimethylphenyl-amino-N-phenyl-methylpropanate

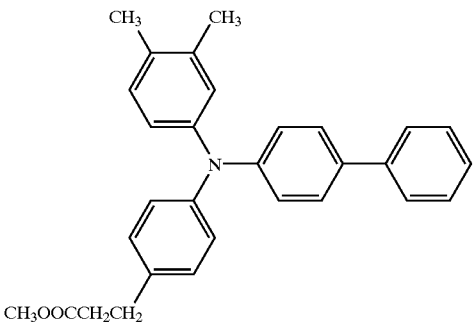

Into a 3-neck 250 milliliters round-bottomed flask equipped with a condenser was placed a mixture of 14.50 grams (0.05 mol) of 4-Iodo-methyl hydrocinnamate, 13.67 grams (0.05 mol) of N-dimethylphenyl-N-biphenylamine, 0.6242 gram (0.0025 mol) of $CuSO_4.5H_2O$, 6.910 gram (0.05 mol) of potassium carbonate, and 10 milliliters of tridecane in a nitrogen atmosphere. The mixture was heated at 230° C. for 20 hours. After the mixture was cooled to room temperature, about 100 milliliters of hexane were added and the solid resulting was collected by filtration. The above solid product was washed with dilute hydrochloric acid and water, filtered, dried at 60° C. overnight, about 18 to 20 hours, resulting in 17.42 grams, 80 percent, yield of product resulted.

N-Biphenyl-N-dimethylphenyl-amino-N-phenyl-propanol

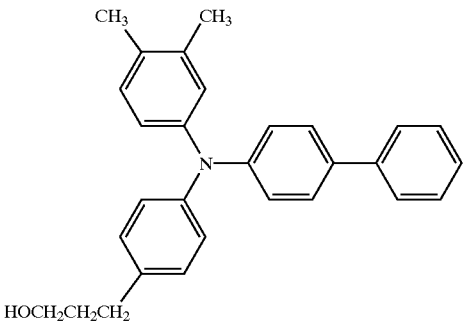

N-biphenyl-N-dimethylphenyl-amino-N-phenyl-methylpropanate (8.71 grams, 0.02 mol) was dissolved in 150 milliliters of tetrahydrofuran in a 3-neck 250 milliliter round-bottomed flask under a nitrogen atmosphere, followed by the slow addition of 0.500 gram (0.013 mol) of lithium aluminum hydride. The mixture was stirred at room temperature (25° C.) for 3 hours, followed by the addition of 1 milliliter of ethyl acetate and 10 milliliters of diluted hydrochloric acid. The resulting slurry was filtered and the solid was washed with 50 milliliters of tetrahydrofuran. The tetrahydrofuran filtrate was collected. After the filtrate was dried with magnesium sulfate, the excess of solvent was removed by vacuo. The above resulting solid product was purified by chromatography and dried at 60° C. overnight, 18 to 20 hours, resulting in 5.79 grams, 71 percent, yield of product.

EXAMPLE II

Synthesis of Aromatic Amine With Silane Crosslinkable Functionality (Id)

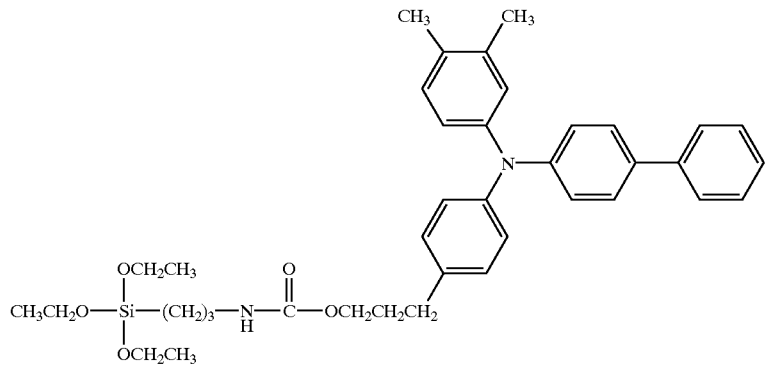

Into a 3-neck 250 milliliter reaction flask was placed a mixture of the electronically pure, about 100 percent, N-biphenyl-N-dimethylphenyl-amino-N-phenyl-propanol (2.50 grams, 6.14 millimoles) and chlorobenzene (15 milliliters) under nitrogen atmosphere. The mixture was stirred and heated at 60° C. until the solid dissolved completely. 3-Isocyanatopropyl triethylsilane (1.75 grams, 7.06 mmoles) was then added to the mixture. The mixture was refluxed for 24 hours. After the reaction mixture was cooled to 25° C., about 150 milliliters of hexane were added, then the mixture was cooled to about −4° C. for 12 hours. The white crystalline product formed was collected by filtration. The above resulting product (Id) with high electronic purity, about 100 percent, was dried in vacuo for 24 hours resulting in 2.88 grams, 71.7 percent, yield of the above product.

EXAMPLE III

Synthesis of Aromatic Amine With Silane Crosslinkable Functionality (II) Biphenyl-N,N'-bis (phenyl-methylpropanate)-1,1'-(biphenyl)-4,4'-diamine

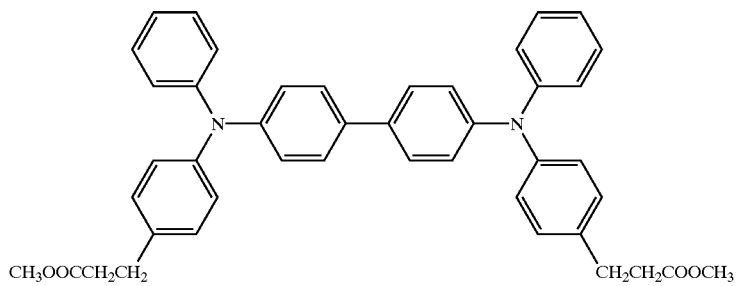

Into a 3-neck 250 milliliter round-bottomed flask equipped with a condenser was placed a mixture of 14.50 grams (0.05 mol) of 4-Iodo-methyl hydrocinnamate, 16.82 grams (0.05 mol) of N,N'-diphenylbenzidine, 0.6242 gram (0.0025 mol) of $CuSO_4.5H_2O$, 6.910 grams (0.05 mol) of potassium carbonate, and 10 milliliters of tridecane in a nitrogen atmosphere. The mixture was heated at 230° C. for 20 hours. After the mixture was cooled to room temperature, about 100 milliliters of hexane were added and the solid was collected by filtration. The solid was washed with dilute hydrochloric acid and water, filtered, dried at 60° C. overnight, 24 hours, resulting in 27.42 grams, 83 percent, yield of the above product.

N,N'-Biphenyl-N,N'-bis(phenylpropanol)-1,1'-(biphenyl)-4,4'-diamine

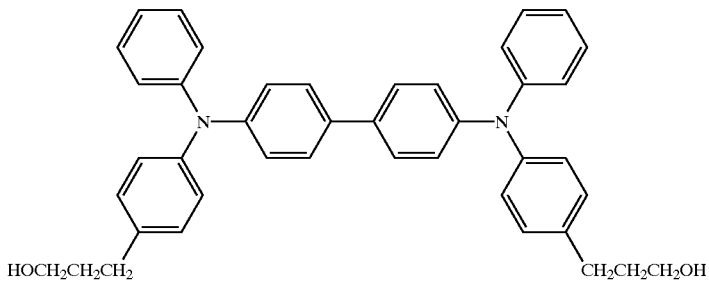

N,N'-Biphenyl-N,N'-bis(phenyl-methylpropanate)-1,1'-(biphenyl)-4,4'-diamine (13.22 grams, 0.02 mol) was dissolved in 200 milliliters of tetrahydrofuran in a 3-neck 500 milliliter round-bottomed flask under a nitrogen atmosphere, followed by the slow addition of 0.800 gram (0.02 mol) of lithium aluminum hydride. The mixture was stirred at room temperature (25° C.) for 5 hours, followed by the addition of 1 milliliter of ethyl acetate and 10 milliliters of diluted hydrochloric acid. The resulting slurry was filtered and the solid was washed with 50 milliliters of tetrahydrofuran. The tetrahydrofuran filtrate was collected and dried with magnesium sulfate. After the excess of tetrahydrofuran solvent was removed by vacuo, the resulting above solid product was purified by chromatography and dried at 60° C. overnight to provide 8.89 grams, 73.5 percent, yield of the above product.

The Aromatic Amine With Silane Crosslinkable Functionality (II)

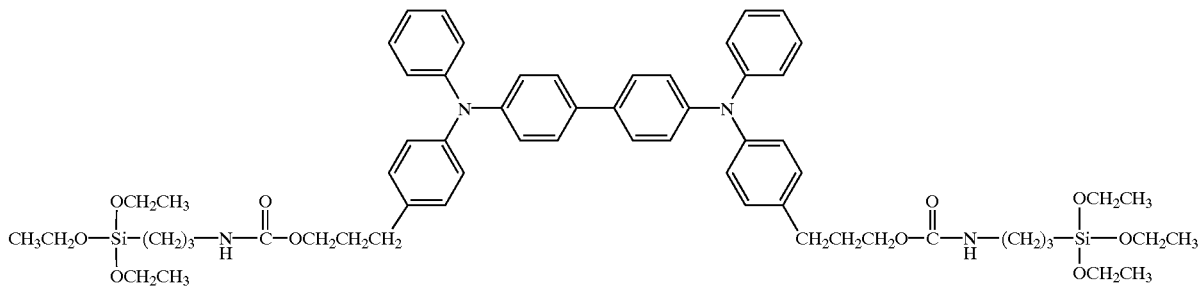

Into a 3-neck 250 milliliter reaction flask was placed a mixture of the electronically pure N,N'-biphenyl-N,N'-bis(phenylpropanol)-1,1'-(biphenyl)-4,4'-diamine (3.02 grams, 5.00 millimoles) and chlorobenzene (15 milliliters) under a nitrogen atmosphere. The mixture was stirred and heated at 60° C. until the solid dissolved completely. 3-Isocyanatopropyltriethylsilane (1.42 grams, 5.75 millimoles) was then added to the mixture. The mixture was refluxed for 24 hours. After the reaction mixture was cooled to 25° C., about 150 milliliters of hexane were added, then the mixture was cooled to about −4° C. for 12 hours. The white crystalline product formed was collected by filtration. The resulting above product (Id) with electronic purity was dried in vacuo for 24 hours to provide 3.97 grams, 72.3 percent, yield of product.

EXAMPLE IV

Preparation of a Thin Film Containing Aromatic Amine With Silane Crosslinkable Functionality (Id), as Shown in Scheme 2

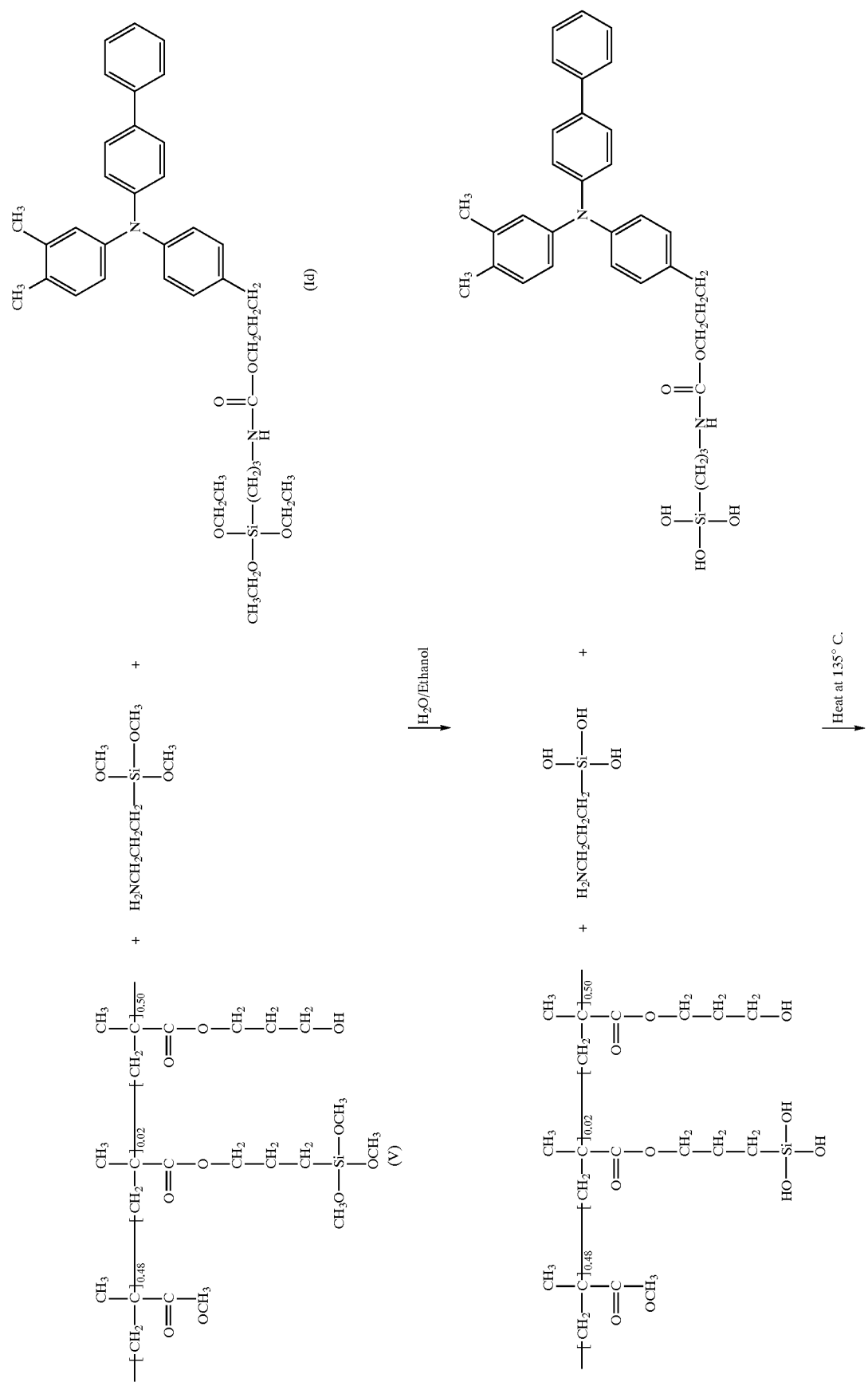

-continued
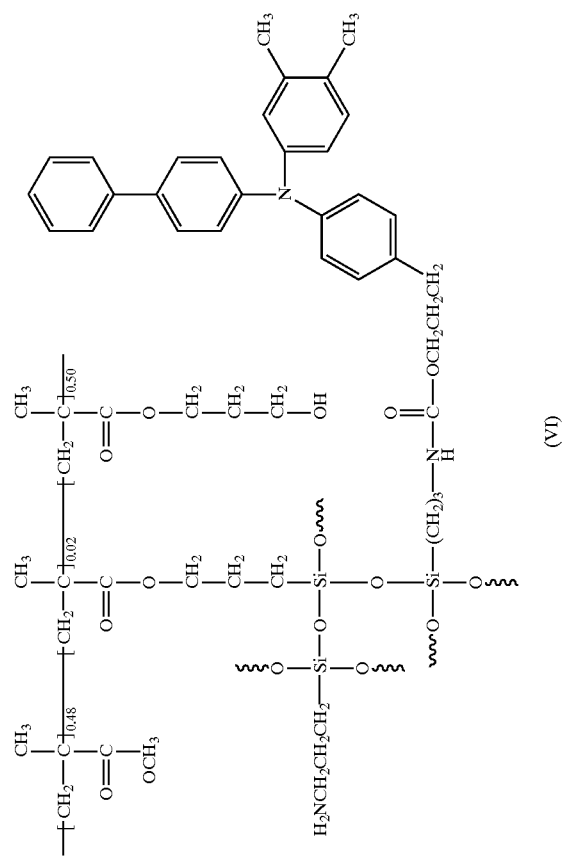
(VI)

A thin film containing an aromatic amine with silane crosslinkable functionality was prepared by the following procedure. A mixture of 0.80 gram of the aromatic amine with silane crosslinkable functionality (Id), 0.80 gram of silane containing polymer binder (V) and 0.40 gram of 3-aminopropyltrimethoxysilane was stirred in 8 grams of a 98.5/1.50 (by weight percent) mixture of ethanol/water at room temperature overnight. The solution was coated on the surface of a photoreceptor device. After coating, the resulting device was dried and cured at 135° C. for about 15 minutes to provide a thin film layer of (VI) Scheme 2. The cured hole transporting thin film layer exhibited excellent resistance to common organic solvents, such as methylenechloride, methanol, ethanol and the like, and there resulted substantially no abrasive to the resulting photoconductive member after 500,000 imaging cycles, and when the crosslinked hole transporting layer can be applied on the surface of a CGL, charge generating layer, or a CTL, charge transport layer, as a crosslinked CTL, or overcoating layer.

Other embodiments and modifications of the present invention may occur to those skilled in the art subsequent to a review of the information presented herein; these embodiments and modifications, equivalents thereof, substantial equivalents thereof, or similar equivalents thereof are also included within the scope of this invention.

What is claimed is:

1. A photoconductive imaging member comprised of a photogenerating layer and charge transport composition comprised of a hole transport segment of Formula (IV)

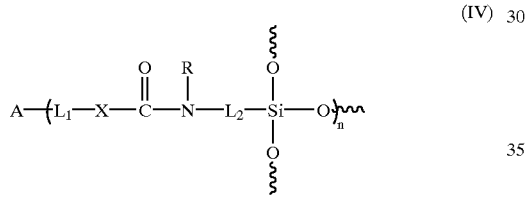

(IV)

wherein A represents a hole transporting aromatic tertiary amine moiety; $L_1$ and $L_2$ represents a divalent group of an alkylene; X represents oxygen or an imino group; R is a hydrogen atom or an alkyl group; and n represents the number of repeating segments, and wherein A is selected from the group consisting of

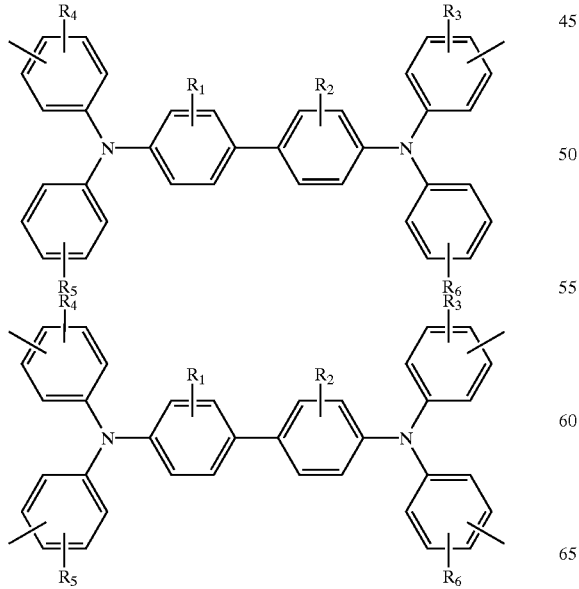

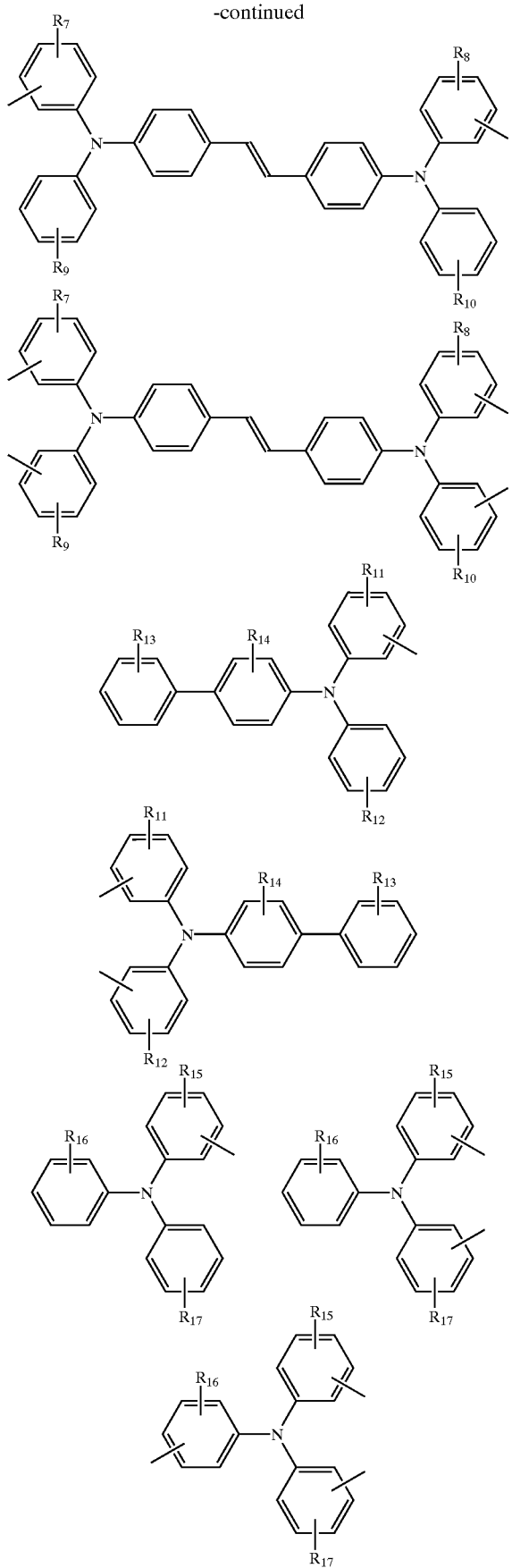

-continued

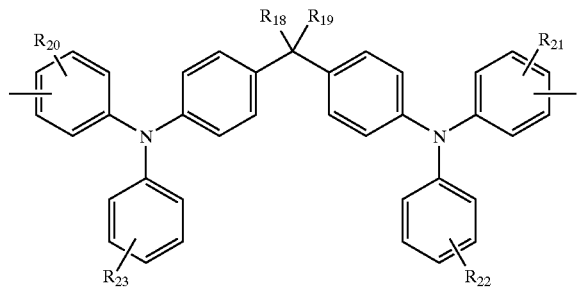

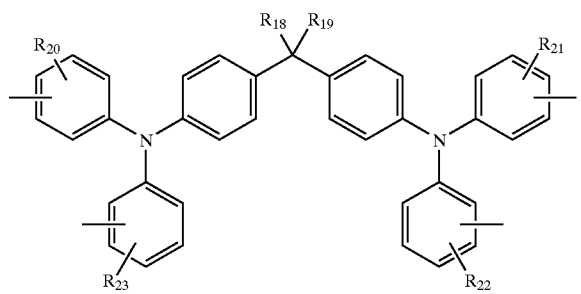

wherein $R_1$ to $R_{23}$ are independently a hydrogen atom, an alkyl, an alkoxyl, or a halogen.

2. A member in accordance with claim 1 wherein $L_1$ and $L_2$ are independently selected from the group consisting of methylene, ethylene, propylene, butylene and pentylene.

3. A member in accordance with claim 1 wherein said alkyl contains from 1 to about 12 carbon atoms, said alkoxy contains from 1 to about 7 carbon atoms, and optionally further wherein said alkyl can be a cyclic alkyl with from 1 to about 12 carbon atoms.

4. A member in accordance with claim 1 wherein X is an oxygen atom, or wherein X is an imino group, and wherein R is a hydrogen atom.

5. An imaging member in accordance with claim 1 wherein said photogenerating layer is comprised of photogenerating pigments of metal phthalocyanines, metal-free phthalocyanines, perylenes, titanyl phthalocyanines, selenium, or hydroxygallium phthalocyanines.

6. A photoconductive imaging member comprised of a photogenerating layer and a charge transport layer, and wherein the charge transport layer is comprised of a hole transport composition comprised of an amine of Formula (IV)

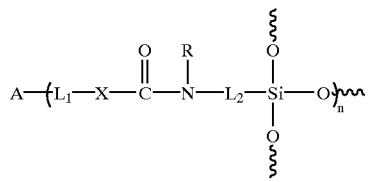

(IV)

wherein A represents a charge transporting aromatic tertiary amine moiety; $L_1$ and $L_2$ represents a divalent group of an alkylene, with from 1 to about 10 carbon atoms; X represents an oxygen or an imino group; R is a hydrogen atom or an alkyl group optionally with from 1 to about 5 carbon atoms; and n is a number, and wherein A is selected from the group consisting of

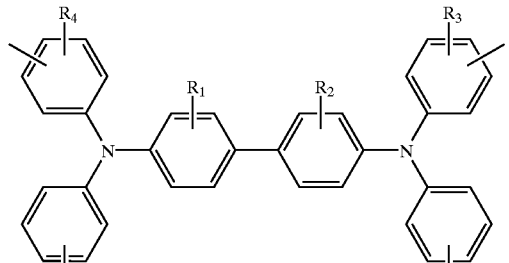

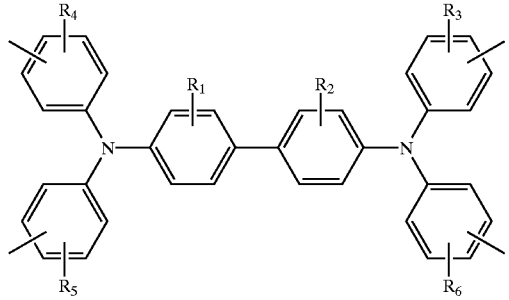

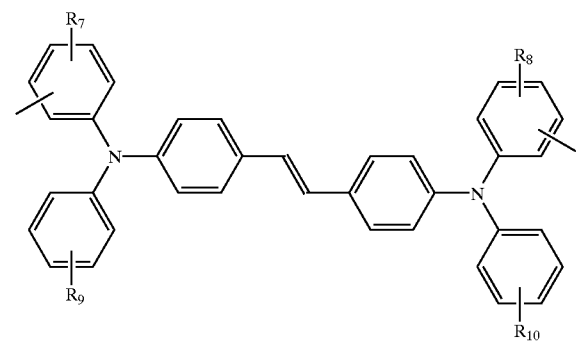

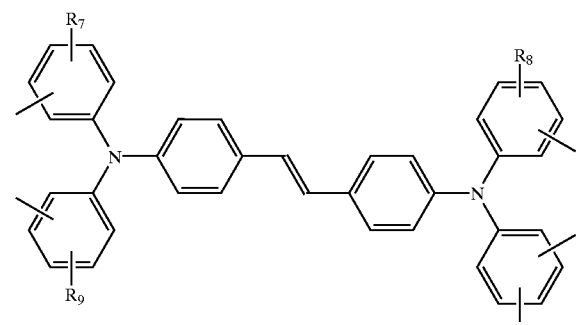

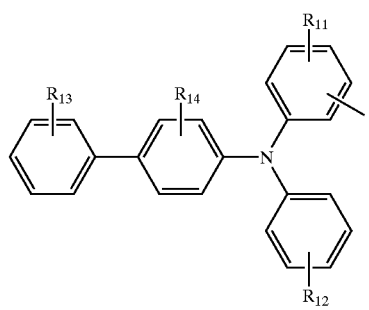

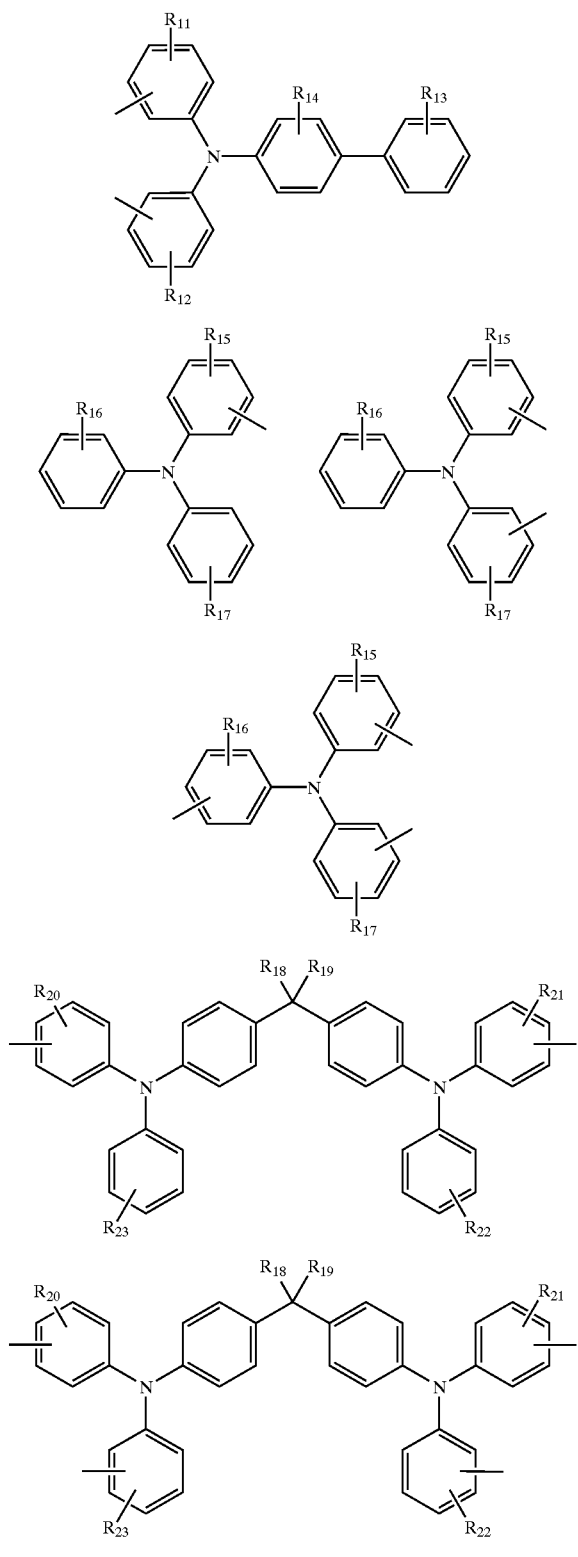

wherein $R_1$ to $R_{23}$ are independently a hydrogen atom, an alkyl, an alkoxyl group, or a halogen.

7. A photoconductive imaging member in accordance with claim 6 wherein $L_1$ and $L_2$ are independently selected from the group consisting of methylene, ethylene, propylene, butylene and pentylene, and n is from 1 to about 5.

8. A photoconductive imaging member in accordance with claim 7 wherein said photogenerating layer is comprised of photogenerating pigments of metal phthalocyanines, metal free phthalocyanines, perylenes, titanyl phthalocyanines, selenium, or hydroxygallium phthalocyanines optionally dispersed in a resin binder.

9. A photoconductive imaging member in accordance with claim 7 and containing a supporting substrate in contact with the photogenerating layer, or containing a supporting substrate in contact with the charge transport layer.

10. A photoconductive imaging member in accordance with claim 7 wherein the supporting substrate is a metal, a conductive polymer, or an insulating polymer, each with a thickness of from about 30 microns to about 300 microns optionally overcoated with an electrically conductive layer with an optional thickness of from about 0.01 micron to about 1 micron, and wherein there is further optionally included an overcoating polymer top layer on said member.

11. A photoconductive imaging member in accordance with claim 7 wherein the photogenerating layer is of a thickness of from about 0.2 to about 10 microns, wherein the charge transport layer is of a thickness of from about 10 to about 100 microns, and wherein there is included a supporting substrate overcoated with a polymeric adhesive layer of a thickness of from about 0.01 to about 1 micron.

12. A photoconductive imaging member in accordance with claim 6 wherein said alkyl contains from 1 to about 10 carbon atoms, said alkoxy contains from 1 to about 5 carbon atoms, and optionally wherein said alkyl is a cyclic alkyl with from 1 to about 10 carbon atoms.

13. A photoconductive imaging member in accordance with claim 6 wherein X is an oxygen atom, or wherein X is an imino group, and wherein R is a hydrogen atom.

14. A photoconductive imaging member in accordance with claim 6 wherein said composition is comprised of the condensation reaction product of
   a) a tertiary amine of Formula (I),
   b) a crosslinkable silane component, and
   c) an optional polymer binder.

15. A photoconductive imaging member in accordance with claim 14 wherein said silane is selected from the group consisting of tetraethoxysilane, 3-aminopropyltrimethoxysilane, 3-aminopropyl triethoxysilane, 3-aminopropyltriisopropoxysilane, 1,2-bis(trimethoxysilyl)ethane, and 1,2-bis(triethoxysilyl)ethane.

16. A photoconductive imaging member in accordance with claim 14 wherein said polymer binder is comprised of

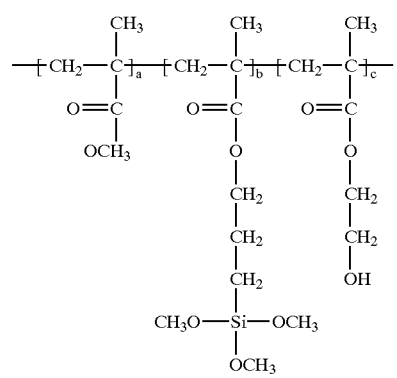

* * * * *